(12) United States Patent
Koseki

(10) Patent No.: US 7,244,260 B2
(45) Date of Patent: Jul. 17, 2007

(54) APPARATUS FOR HOLDING AND ARRANGING THREADS IN SURGICAL OPERATIONS

(75) Inventor: Tomoaki Koseki, Toshima-ku (JP)

(73) Assignee: Kosek Medical K.K., Tokyo (JP)

( * ) Notice: Subject to any disclaimer, the term of this patent is extended or adjusted under 35 U.S.C. 154(b) by 568 days.

(21) Appl. No.: 10/243,696

(22) Filed: Sep. 14, 2002

(65) Prior Publication Data
US 2003/0055439 A1    Mar. 20, 2003

(30) Foreign Application Priority Data
Sep. 18, 2001   (JP) .............................. 2001-283775

(51) Int. Cl.
A61B 17/04   (2006.01)
A61B 1/32    (2006.01)
(52) U.S. Cl. ...................................... 606/148; 600/233
(58) Field of Classification Search ................ 606/148, 606/144, 147, 103, 151; 600/229, 233, 206
See application file for complete search history.

(56) References Cited
U.S. PATENT DOCUMENTS 3,515,129 A * 6/1970 Truhan ....................... 600/206
4,274,398 A * 6/1981 Scott, Jr. .................... 600/233
4,434,791 A * 3/1984 Darnell ....................... 600/233
5,951,467 A * 9/1999 Picha et al. ................. 600/233

FOREIGN PATENT DOCUMENTS

JP   8-501002    2/1996
JP   2000-225118  8/2000

* cited by examiner

Primary Examiner—Julian W. Woo

(57) ABSTRACT

An apparatus for holding and arranging threads in surgical operations with a flexible structure being in a ring form, connecting straight linear forms or divided linear forms, with flexible metal inserted within foaming material. V shape ditches are cut on the upper portion, and the base has adhesiveness. Affordable and simple manufacturing method is established with extrusion molding process or heat press molding process, after which extrusion cut process is conducted with the mold. Labor within hospitals can be reduced, by providing an affordable apparatus which prevents the threads from being damaged, also solving the concern of tissue damage due to thread tension, as the threads are accurately held and arranged without any mixing up with neighboring threads, and the apparatus size, the fixing position of the apparatus, and the operating tissue area can be adjusted at the surgeon's will.

2 Claims, 3 Drawing Sheets

APPARATUS FOR HOLDING AND ARRANGING THREADS IN SURGICAL OPERATIONS

BACKGROUND OF THE INVENTION

1. Field of the Invention

This invention relates to apparatus for temporarily holding and arranging surgical threads utilized during surgical operations.

2. Description of the Prior Art

Conventionally, the end of a thread is either directly held with non-hook forceps such as Péan's forceps or mosquito forceps, or by holding the thread after placing short cut pieces of rubber tubes such as Nelaton on the tip of forceps to protect the thread.

SUMMARY OF THE INVENTION

The grasp part at the end of forceps has horizontal ditches to hold and grasp the tissue to facilitate the grasping, as grasping is the forceps' primary function. When a surgeon tries to hold a piece of thread with such forceps, the thread surface is damaged, the tension of the thread is reduced significantly and therefore such a practice is not preferred. When applying rubber tubes such as Nelaton on the tip of forceps, the thread surface is protected, but that would increase the labor of hand-washing nurses. In operations for heart valve substitution and such, 12 to 20 pieces of threads are utilized for stitching the valve rim. In operations for substitution of mitralis valve or aorta valve in one operation, a maximum of 40 pieces of threads are utilized. In such a case, 40 forceps are to be prepared, the used forceps need to be washed and re-sterilized for the next operation. As the tip of the forceps are divided in two, 80 rubber tubes needs to be prepared in such cases. In an economical environment where hospital management is in a severe situation, it is preferable to minimize the volume of materials and labor required.

Also when fixing an end of a thread with forceps, the weight of the forceps loads on the thread, and the thread pulls the stitched tissue. Some tension on thread is required to prevent each thread from mixing up with each other, but as the stitched part is often a diseased and frail tissue, there are possibilities for the stitched tissue to be torn from the thread tension. Furthermore, many forceps hang at the edge part of operating tissue area, which is an obstacle for the operation. When the order of forceps change, neighboring threads may be mixed up.

In a case where the apparatus for holding arranging threads is a ring shape form the outset, manufacture, sterilization, packaging and storage require a large cubic volume, and could be inconvenient. When there is a straight linear form and a ring shape can be made by snapping together several of the protrusions and indentations on both ends and the ring circumference is adjustable by the number of connected protrusions and indentations, a shipment package can be in a compact rectangular form reduce the manufacturing and distribution cost. This invention is useful in valve substitution operations in cardiac surgery or in septum deficient repair operations in pediatric cardiac surgery, wherein the body size of patients vary largely, and in such a situation, when the shape of this apparatus is fixed in a ring shape, many items of products of various types and sizes will be necessary as the product standard. When the apparatus is made in a straight linear shape enabling connections to be made, the product can be standardized as one item, largely contributing to cost reduction.

The upper portion of the main part where threads enter is narrowed at the top in a tapered form, and cuts a applied in pairs. The top part of each cut is made into a V-shape ditch and a structure is made wherein a thread enters easily. The lowered portion of the main part has a hole for allowing cloth forceps to fix the apparatus to a covering sheet.

When a flexible metal like aluminum or wire is inserted into the main part, the size and shape of the operative field adapts flexibly, and the product can be standardized as one item, largely contributing to cost reduction.

DETAILED DESCRIPTION OF THE INVENTION

Hereafter, a description of the preferred embodiments of this invention is made in reference to drawings. FIG. 1 shows a ring shape apparatus for holding and arranging threads in surgical operations claimed in claim 1. The upper portion 2 of the main part of the ring form being narrowed at the top in a tapered form with pairs of cuts made continuously in vertical angle in relation to the ring shown as cut 3 to hold and maintain the thread, V shape ditch 4 applied at the top part of each cut, the lower portion of the main part having a hole 5 for cloth forceps to fix this apparatus on a covering sheet. The manufacturing method for this apparatus is extrusion molding method as described in claim 3, extruding flexible material such as vinyl chloride or polyethylene foam which does not damage the thread surface, and then cut in determined size. Cut 3, V shape ditch 4, hole 5 for cloth forceps are extruded and cut with the mold the main part being in a straight linear form. When cut 3 is made in pairs, it is very convenient for the surgeon to prevent mixing up of neighboring threads when different color threads such as white and blue are used alternately.

FIG. 2 shows the apparatus for holding and arranging surgical threads, wherein the Main part 1 has a straight linear form, and makes a ring shape by snapping protrusions and indentations at the end. The structure allows for adjustment at the protrusions and indentations to enable changes to the size of the ring circumference. One end of the main part has protrusion 6, and the other end has hole 7 to insert over the protrusion. When both ends are connected to each other, a small ring form is realized, and when many main parts are connected, a larger ring can be formed. Furthermore, by connecting and disconnecting the protrusion 6 and hole 7 are in the same size, the center disturbing the operating tissue area, the upper portion of the main part of the ring form.

FIG. 3 shows the linear apparatus for holding and arranging surgical threads, divided into sections. The upper portion of the main part being narrowed at the top in a tapered form with cut 3 in pairs of cuts made continuously to hold and maintain the thread, and a V shape ditch is applied at the top part of each cut. The material of the main part is a foaming material specifically being acrylic foam, and the main part can be fixed on the surface of a heart opening instrument by adhering the back side on top of the heart opening instrument. The apparatus is manufactured with a process of placing flexible metal between two acrylic foam sheets, applying heat and pressure from the outside of the foaming material to mold it into shape, and using a press mold to make cuts and V-shaped ditches from the side.

It is convenient for cut 1 to be made in pairs, to prevent mixing up of neighboring threads when different colored threads such as white and blue are utilized alternately. The V shape ditch guides the thread into cut 1 accurately.

FIG. 4 is a cross sectional diagram of the apparatus, showing how flexible metal like aluminum is inserted in the foaming material. This apparatus enables the surgeon to bend the apparatus in a desired curve.

This invention has the following effects, conducted as in the above description.

This invention reduces labor in hospitals, by providing an affordable apparatus for holding surgical threads precisely without damaging the thread, and without any concern of tissue damage due to thread tension.

The ring form does not disturb the operating tissue area. When the cuts are in pairs, it is convenient in prevention mixing up of neighboring threads when using different colored thread such as white and blue used alternately.

Manufacture, sterilization, packaging, and storage of ring shape apparatuses require a large cubic volume, and could be inconvenient. The ring shape can be realized by connecting main parts made in straight linear forms, a linear form having projections and holes at each end, enabling a structure to adjust and change the ring circumference by connecting and disconnecting the projections and holes, thus a shipment package can be in a compact rectangular form rather than a large square, reducing the whole cubic volume, making it possible to reduce the manufacturing and distribution cost. Also, this apparatus is useful in valve substitution operations in cardiac surgeries or in septum deficient repair operations in pediatric cardiac surgeries, wherein the body size of patients vary largely, and in such a situation, when the shape of this apparatus is fixed in a ring shape, many items of products in a various types and sizes are necessary. When the apparatus is made in a straight linear shape enabling connection to make a ring to make a ring form, the product can be standardized as one item, largely contributing to cost reduction.

The apparatus in claim 1 and 2 can be manufactured with extrusion molding method, wherein the material is extruded, cut in determined size, cut from the side with the extrusion mold to simultaneously cut out the V shape ditch and the hole for the cloth forceps, and affordable products can be provided.

Flexible metal such as wire or aluminum is inserted inside the straight linear shape main part foaming material, the apparatus can be flexibly adjusted to the shape and size of the operating tissue area, standardization of the product can be conducted with one item of product, and would largely contribute to cost reduction.

The surface of this acrylic foaming material has individual cell air bubble structure, having suction effect with appropriate adhesiveness. This material can be fixed by adhering onto heart opening instruments and such. This material has higher adhesiveness compared to other adhesives such as dual-face tapes, and has no stickiness, and is easier to peel off.

The manufacturing method for the apparatus is a process in which the form is molded by having flexible metal such as wire or aluminum inserted between two plates molded of foaming material, heat and pressure applied to the outside of the foaming material mold, and cuts from the side with the extrusion mold are made to cut out the V shape ditch and hole for the cloth forceps simultaneously.

Figure 1:
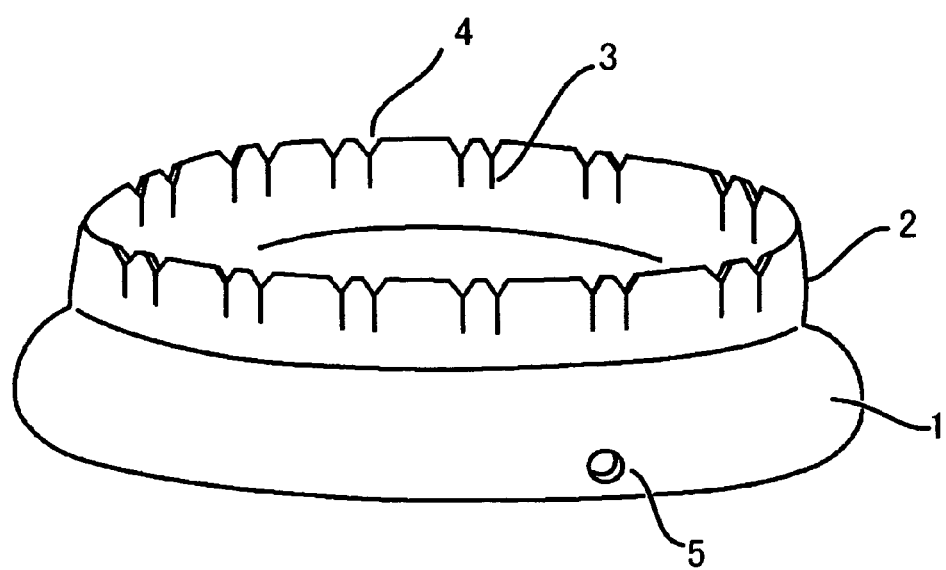
FIG. 1 is a cross-sectional and external diagram of an apparatus for holding and arranging threads in surgical operations.
Figure 2:
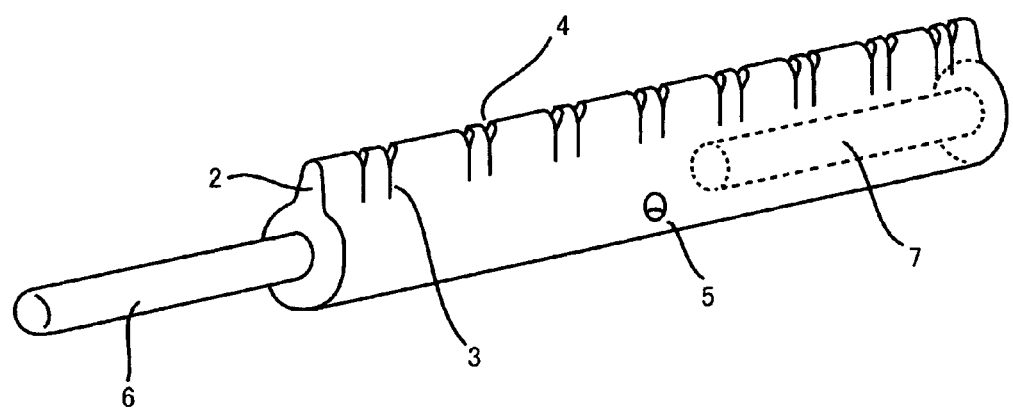
FIG. 2 shows external diagram of a connecting type apparatus for holding and arranging threads in surgical operations.
Figure 3:
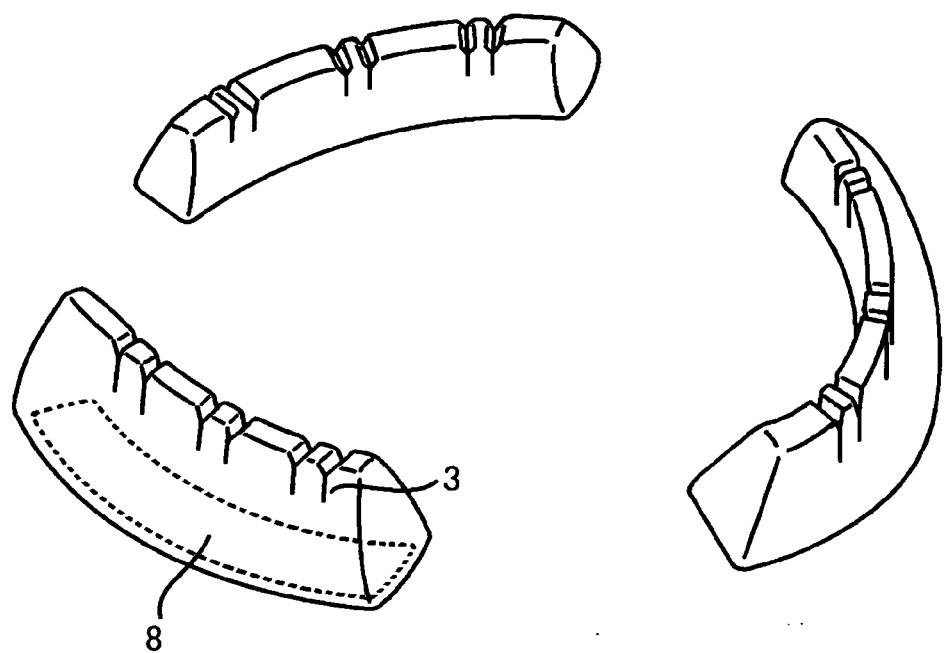
FIG. 3 is an external diagram of a divided type apparatus for holding and arranging threads in surgical operations.
Figure 4:
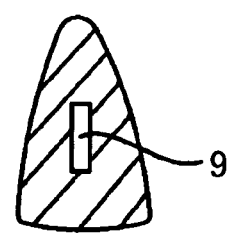
FIG. 4 is a cross-sectional and external diagram of a divided type apparatus for holding and arranging threads in surgical operations.

What is claimed is:

1. An apparatus for holding and arranging threads in surgical operations, the apparatus comprising a main body comprising a straight linear form having at least one protrusion on one end, and at least one corresponding indentation on another end, wherein each protrusion and each indentation are configured to be joined together to form the main body into a ring form comprising an upper portion and a lower portion, wherein the circumference of the ring form is adjustable by movement of a protrusion with respect to its corresponding indentation wherein the upper portion is narrowed in a tapered form and has a plurality of pair of cuts for holding and maintaining the threads the cuts being made in a vertical angle with respect to the ring form, wherein a V-shaped ditch is applied to a top part of each cut, and wherein the lower portion has a hole for allowing cloth forceps to fix the apparatus to a covering sheet.

2. An apparatus for holding and arranging threads in surgical operations, the apparatus comprising a main part having a straight linear form with a longitudinal axis and an upper portion, the upper portion being narrowed in a tapered form and having a plurality of pairs of cuts for holding and maintaining the threads, the cuts being made at a vertical angle with respect to the longitudinal axis wherein a V-shaped ditch is applied at a top part of each cut, and wherein the main part is formed from a foam material and a flexible metal wire inserted within the foam material, such that a surgeon is enabled to bend the apparatus into a desired curve.

* * * * *